United States Patent
Chinta (10) Patent No.: US 8,946,495 B2
(45) Date of Patent: Feb. 3, 2015

(54) PROCESS FOR ALKYLATION OF TOLUENE TO FORM STYRENE AND ETHYLBENZENE

(75) Inventor: Sivadinarayana Chinta, Missouri City, TX (US)

(73) Assignee: Fina Technology, Inc., Houston, TX (US)

(*) Notice: Subject to any disclaimer, the term of this patent is extended or adjusted under 35 U.S.C. 154(b) by 168 days.

(21) Appl. No.: 13/457,494

(22) Filed: Apr. 27, 2012

(65) Prior Publication Data

US 2012/0296136 A1 Nov. 22, 2012

Related U.S. Application Data

(60) Provisional application No. 61/488,771, filed on May 22, 2011.

(51) Int. Cl.
*C07C 1/207* (2006.01)
*C07C 2/66* (2006.01)
*B01J 8/04* (2006.01)
*C07C 2/86* (2006.01)

(52) U.S. Cl.
CPC ............ *B01J 8/0465* (2013.01); *C07C 2/864* (2013.01); *C07C 2/865* (2013.01); *C07C 2/867* (2013.01); *B01J 8/0488* (2013.01); *C07C 2521/02* (2013.01); *C07C 2521/06* (2013.01); *C07C 2523/02* (2013.01); *C07C 2523/04* (2013.01); *C07C 2523/08* (2013.01); *C07C 2523/12* (2013.01); *C07C 2523/20* (2013.01); *C07C 2523/22* (2013.01); *C07C 2523/28* (2013.01); *C07C 2523/34* (2013.01); *C07C 2523/50* (2013.01); *C07C 2523/72* (2013.01); *C07C 2523/745* (2013.01); *C07C 2523/75* (2013.01); *C07C 2529/08* (2013.01); *B01J 2219/00006* (2013.01); *B01J 2219/00038* (2013.01); *B01J 2219/0004* (2013.01)
USPC ............................ 585/435; 585/467; 585/469

(58) Field of Classification Search
CPC ......... C07C 2/864; C07C 2/865; C07C 2/967; C07C 2/66; C07C 15/46
USPC .......................................... 585/435, 467, 469
See application file for complete search history.

(56) References Cited

U.S. PATENT DOCUMENTS

| | | | |
|---|---|---|---|
| 3,755,483 A | 8/1973 | Burress | |
| 4,140,726 A * | 2/1979 | Unland et al. | 585/438 |
| 4,479,024 A | 10/1984 | Bruylants et al. | |
| 4,499,318 A | 2/1985 | Liu | |
| 6,958,135 B1 * | 10/2005 | Filippi et al. | 422/198 |
| 2008/0262281 A1 | 10/2008 | Walsdorff et al. | |
| 2009/0247801 A1 | 10/2009 | Butler | |
| 2010/0168486 A1 | 7/2010 | Butler et al. | |
| 2011/0257451 A1 | 10/2011 | Thorman et al. | |

FOREIGN PATENT DOCUMENTS

JP 60097922 A 5/1985

* cited by examiner

*Primary Examiner* — Thuan D Dang (57) ABSTRACT

A process is disclosed for making styrene and/or ethylbenzene by reacting toluene with a $C_1$ source over a catalyst in at least one radial reactor to form a product stream comprising styrene and/or ethylbenzene.

15 Claims, 5 Drawing Sheets

PROCESS FOR ALKYLATION OF TOLUENE TO FORM STYRENE AND ETHYLBENZENE

CROSS-REFERENCE TO RELATED APPLICATIONS

This application claims priority to U.S. Provisional Patent No. 61/488,771 filed on May 22, 2011.

FIELD

The present invention relates to a method for the production of styrene and ethylbenzene. More specifically, the invention relates to the use of a radial reactor for the alkylation of toluene with methanol and/or formaldehyde to produce styrene and ethylbenzene.

BACKGROUND

Styrene is a monomer used in the manufacture of many plastics. Styrene is commonly produced by making ethylbenzene, which is then dehydrogenated to produce styrene. Ethylbenzene is typically formed by one or more aromatic conversion processes involving the alkylation of benzene.

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and reduced polyalkylated content. When both alkylation and transalkylation processes are used, two separate reactors, each with its own catalyst, can be employed for each of the processes.

Ethylene is obtained predominantly from the thermal cracking of hydrocarbons, such as ethane, propane, butane, or naphtha. Ethylene can also be produced and recovered from various refinery processes. Thermal cracking and separation technologies for the production of relatively pure ethylene can account for a significant portion of the total ethylbenzene production costs.

Benzene can be obtained from the hydrodealkylation of toluene that involves heating a mixture of toluene with excess hydrogen to elevated temperatures (for example 500° C. to 600° C.) in the presence of a catalyst. Under these conditions, toluene can undergo dealkylation according to the chemical equation: $C_6H_5CH_3+H_2 \rightarrow C_6H_6+CH_4$. This reaction requires energy input and as can be seen from the above equation, produces methane as a byproduct, which is typically separated and may be used as heating fuel for the process.

Other known process include the alkylation of toluene to produce styrene and ethylbenzene. In this alkylation process, various aluminosilicate catalysts are utilized to react methanol and toluene to produce styrene and ethylbenzene. However, such processes have been characterized by having very low yields in addition to having very low selectivity to styrene and ethylbenzene.

Additionally, it is known that the alkylation of toluene with methanol to produce styrene and ethylbenzene is a dehydrogenation reaction, which occurs efficiently at low pressures. Conversely, at high pressure, hydrogenation may occur, and the produced styrene may be hydrogenated to ethylbenzene. This hydrogenation reaction is undesirable in the production of styrene. Furthermore, it is known that pressure drop over the catalyst and the time that the reactants are in contact with the catalyst, commonly referred to as the "contact time," are linearly related. As the length of contact time increases in the reactor, the likelihood of undesirable reactions, such as the hydrogenation of styrene to ethylbenzene, increases.

In view of the above, it would be desirable to have a process of producing styrene and/or ethylbenzene that does not rely on thermal crackers and expensive separation technologies as a source of ethylene. It would further be desirable to avoid the process of converting toluene to benzene with its inherent expense and loss of a carbon atom to form methane. It would be desirable to produce styrene without the use of benzene and ethylene as feedstreams. It would also be desirable to produce styrene at low pressure and with minimal contact time to increase the efficiency of the production of styrene and to reduce undesirable reactions, such as hydrogenation of styrene to ethylbenzene. Furthermore, it is desirable to have a reactor system able to achieve a high yield and selectivity to styrene and ethylbenzene.

SUMMARY

An embodiment of the present invention is a process for making styrene and/or ethylbenzene by reacting toluene with a $C_1$ source over a catalyst in at least one radial reactor to form a product stream comprising styrene. In an embodiment the $C_1$ source is selected from the group of methanol, formaldehyde, formalin, trioxane, methylformcel, paraformaldehyde, methylal, dimethyl ether, and combinations thereof.

In an embodiment, either by itself or in combination with any other embodiment, the reaction pressure in the radial reactor can range from 0.1 atm to 70 atm, optionally from 0.1 atm to 10 atm, and optionally from 0.1 atm to 5 atm. The radial reactor can include a reaction zone including the catalyst and the process is conducted such that the average residence time in the reaction zone of the reactants is less than 10 minutes, optionally less than 5 minutes, optionally less than 30 seconds.

In an embodiment, either by itself or in combination with any other embodiment, the catalyst is based on a zeolite selected from the group consisting of faujasites. Optionally, the catalyst is based on an X-type zeolite. The catalyst can be promoted with a promoter selected from the group of Co, Mn, Ti, Zr, V, Nb, K, Cs, Ga, B, P, Rb, Ag, Na, Cu, Mg, Fe, Mo, Ce, or combinations thereof. In an embodiment, the zeolite can be promoted with one or more of Ce, Cu, P, Cs, B, Co, Ga, or combinations thereof.

Another embodiment of the present invention, a process for making styrene and ethylbenzene includes forming from a $C_1$ source a first product stream including formaldehyde, the first product stream formed in one or more first reactors, and reacting toluene with the first product stream in at least one radial reactor to form a second product stream including one or more of styrene or ethylbenzene. The $C_1$ source includes one or more of methanol or formaldehyde.

In an embodiment, either by itself or in combination with any other embodiment, the radial reactor includes a catalyst based on a faujasite framework. The reaction pressure in the radial reactor can be in the range of about 0.1 atm to about 5 atm. The radial reactor can include a reaction zone including the catalyst and the process can be conducted such that the average residence time in the reaction zone of the reactants is less than about 60 seconds.

In an embodiment, either by itself or in combination with any other embodiment, the catalyst is based on an X-type zeolite. The catalyst can be promoted with a promoter selected from the group of Co, Mn, Ti, Zr, V, Nb, K, Cs, Ga, B, P, Rb, Ag, Na, Cu, Mg, Fe, Mo, Ce, or combinations thereof. In an embodiment, the zeolite can be promoted with one or more of Ce, Cu, P, Cs, B, Co, Ga, or combinations thereof.

The various embodiments of the present invention can be joined in combination with other embodiments of the invention and the listed embodiments herein are not meant to limit the invention. All combinations of embodiments of the invention are enabled, even if not given in a particular example herein.

DETAILED DESCRIPTION

In an embodiment of the current invention, toluene is reacted with a carbon source, which can be referred to as a $C_1$ source, over a catalyst in at least one radial reactor to produce styrene and ethylbenzene. In an embodiment, the $C_1$ source includes methanol or formaldehyde or a mixture of the two. In a further embodiment, the $C_1$ source is selected from the group consisting of methanol, formaldehyde, formalin (37-50% $H_2CO$ in solution of water and MeOH), trioxane (1,3,5-trioxane), methylformcel (55% $H_2CO$ in methanol), paraformaldehyde, methylal (dimethoxymethane), and dimethyl ether, and combinations thereof.

Formaldehyde can be produced either by the oxidation or dehydrogenation of methanol. In an embodiment, formaldehyde is produced by the dehydrogenation of methanol to produce formaldehyde and hydrogen gas. This reaction step produces a dry formaldehyde stream that may be desirable, as it would not require the separation of the water prior to the reaction of the formaldehyde with toluene. Formaldehyde can also be produced by the oxidation of methanol to produce formaldehyde and water.

In the case of using a separate process to obtain formaldehyde, a separation unit may then be used in order to separate the formaldehyde from the hydrogen gas or water from the formaldehyde and unreacted methanol prior to reacting the formaldehyde with toluene for the production of styrene. This separation would inhibit the hydrogenation of the formaldehyde back to methanol. Purified formaldehyde could then be sent to a styrene radial reactor and the unreacted methanol could be recycled.

Although the reaction has a 1:1 molar ratio of toluene and the $C_1$ source, the ratio of the feedstreams is not limited within the present invention and can vary depending on operating conditions and the efficiency of the reaction system. If excess toluene or $C_1$ source is fed to the reaction zone, the unreacted portion can be subsequently separated and recycled back into the process. In one embodiment, the ratio of toluene:$C_1$ source can range from between 100:1 to 1:100. In alternate embodiments, the ratio of toluene:$C_1$ source can range between from 50:1 to 1:50; from 20:1 to 1:20; from 10:1 to 1:10; from 5:1 to 1:5; from 2:1 to 1:2.

Figure 1:
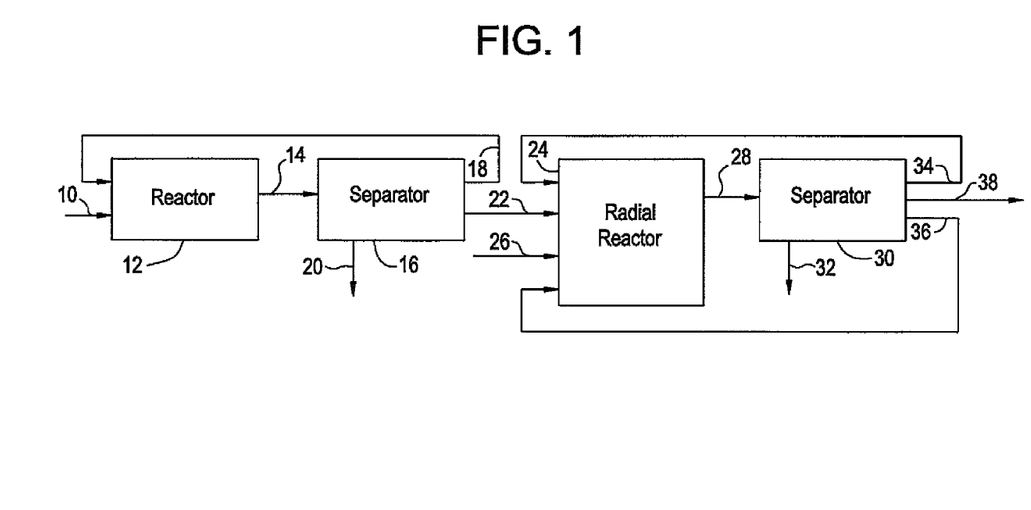
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene in a radial reactor to produce styrene.

In FIG. 1, there is a simplified flow chart of one embodiment of the styrene production process described above. In this embodiment, a first reactor (12) is either a dehydrogenation reactor or an oxidation reactor. The first reactor is designed to convert the first methanol feed (10) into formaldehyde. The gas product (14) of the first reactor is then sent to a gas separation unit (16) where the formaldehyde is separated from any unreacted methanol and unwanted byproducts. Any unreacted methanol (18) can then be recycled back into the first reactor (12). The byproducts (20) are separated from the clean formaldehyde (22).

In one embodiment, the first reactor (12) is a dehydrogenation reactor that produces formaldehyde and hydrogen and the separation unit (16) is a membrane capable of removing hydrogen from the product stream (14).

In an alternate embodiment, the first reactor (12) is an oxidative reactor that produces product stream (14) including formaldehyde and water. The product stream (14) including formaldehyde and water can then be sent to a second reactor (24) without a separation unit (16).

The formaldehyde feed stream (22) is then reacted with a feed stream of toluene (26) in the second reactor (24), which is a radial reactor in the embodiment illustrated in FIG. 1. The toluene and formaldehyde react to produce styrene. The product (28) of the radial reactor (24) may then be sent to an optional separation unit (30) where any unwanted byproducts (32) such as water can be separated from the styrene, unreacted formaldehyde and unreacted toluene. Any unreacted formaldehyde (34) and the unreacted toluene (36) can be recycled back into the radial reactor (24). A styrene product stream (38) can be removed from the separation unit (30) and subjected to further treatment or processing if desired.

Figure 2:
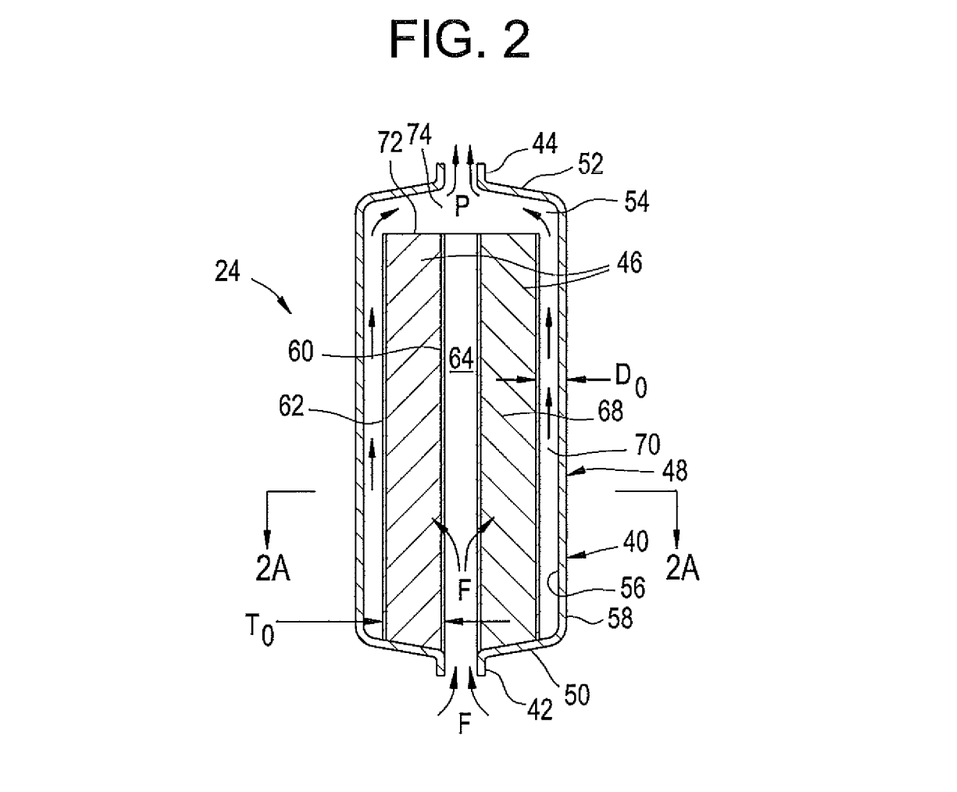
FIG. 2 illustrates a cross-sectional view of a conventional radial reactor capable of producing styrene from the reaction of toluene and formaldehyde consistent with one embodiment of the present invention.
Figure 2A:
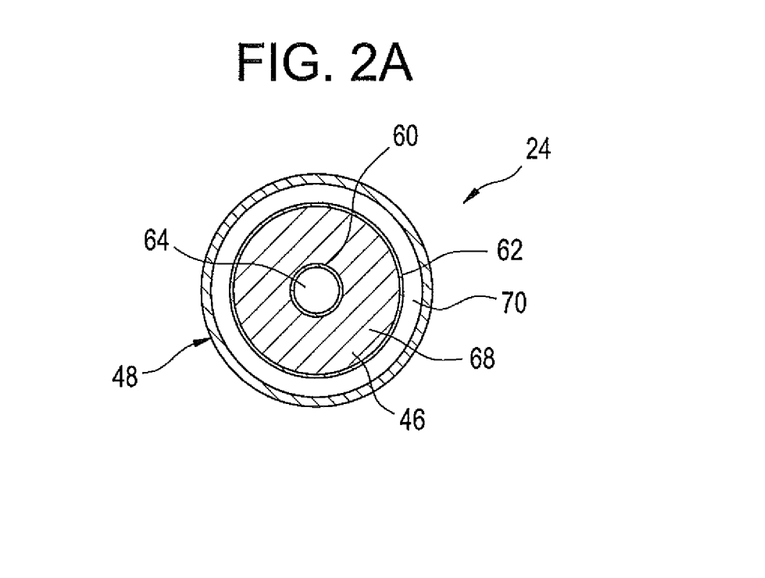
FIG. 2A illustrates a top cross-sectional view along the cutting plane of the embodiment shown in FIG. 2.

FIGS. 2 and 2A illustrate a radial reactor (24) used in one embodiment of the styrene production process. The radial reactor (24) illustrated in FIG. 2 and discussed below is a nonlimiting example, as other radial reactors known in the art may be used based on the system specifications and operator's needs. The radial reactor (24) includes an elongated cylindrical shell (40) that includes an inlet (42) and an outlet (44) and further contains a catalyst bed (46). More specifically, the elongated cylindrical shell (40) comprises a vertical cylindrical sidewall (48) connecting an inlet side portion (50) defining the inlet (42) and an outlet side portion (52) defining the outlet (44). The vertical cylindrical sidewall (48) defines an interior cavity (54) and comprises an internal sidewall surface (56) and an external sidewall surface (58). The inlet side portion (50) defines the inlet (42) such that the inlet allows a feedstream to be fed into the interior cavity (54). The outlet side portion (52) defines the outlet (44) such that the outlet allows a product stream to exit from the interior cavity (54).

As shown in FIGS. 2 and 2A, an inner cavity wall (60) and an outer cavity wall (62) are disposed within the interior cavity (54), and are designed to retain the catalyst bed (46). The inner cavity wall (60) is mounted within the interior cavity (54) so as to create an inner passage (64) and an inner annulus (68) surrounded by the catalyst bed (46), which may comprise one or more layers of catalyst materials. The outer cavity wall (62) is mounted within the interior cavity (54) substantially parallel to the vertical cylindrical sidewall (48) but separated from the cylindrical sidewall by a predetermined distance, ($D_o$), thereby defining an outer annulus (70). The outer cavity wall (62) is also separated from the inner cavity wall (60) by a distance, ($T_o$) to define an inner annulus (68). The inner cavity wall and outer cavity wall are constructed from a porous or perforated material, such that radial flow between the inner cavity wall and outer cavity wall is maximized and the catalyst material is retained within. In one embodiment, the inner cavity wall and outer cavity wall may be formed from screens.

The inner cavity wall (60) and outer cavity wall (62) are secured to the internal sidewall surface (56) of the inlet side portion (50) and extend from the inlet side portion (50) substantially parallel to the cylindrical sidewall (48) toward the outlet side portion (52), but terminate before reaching the internal sidewall surface (56) of the outlet side portion (52). A catalyst bed thickness ($T_o$) is defined as the distance between the inner cavity wall (60) and the outer cavity wall (62). When the catalyst bed (46) is loaded between the inner and outer cavity walls (60, 62), a cover or cap (72) is disposed over the terminated inner and outer cavity walls and catalyst bed proximate the outlet side portion (52). A headspace (74) in fluid communication with the outlet (44) is formed between the cap (72) disposed over the top of the catalyst bed (46) and the outlet side portion (52) of the radial reactor (24). Thus, the outer annulus, headspace, and outlet are all in fluid communication.

As illustrated in FIGS. 2 and 2A, the cap (72) is intended to prevent the feedstream (F) from entering the radial reactor (24) at the inlet (42) and flowing straight through the inner passage (64) and out through the outlet (44). The cap (72) forces the feedstream to flow radially through the inner annulus (68) and catalyst bed (46) and into the outer annulus (70) where the now-treated feedstream, or product stream (P), flows into the headspace (74) and out through the outlet (44). In the embodiment shown in FIGS. 2 and 2A, the catalyst bed (46) comprises a vertical layer (68) comprising catalyst particles. In operation in one embodiment, a fluid feedstream (F), comprising toluene and formaldehyde is fed into the radial reactor (24) though inlet (42) and is forced, via pressure, into the inner passage (64). As additional toluene and formaldehyde is forced into the radial reactor (24) through the inlet (42), the toluene and formaldehyde in the inner passage (64) flows radially though the porous or perforated inner cavity wall (60) and migrates through the inner annulus (68) containing the catalyst particles, and then migrates through the porous or perforated vertical outer cavity wall (62) into the outer annulus (70) as a now-treated feedstream, or product stream (P). The product stream (P) then flows into the headspace (74) and exits the radial reactor (24) through the outlet (44).

Figure 3:
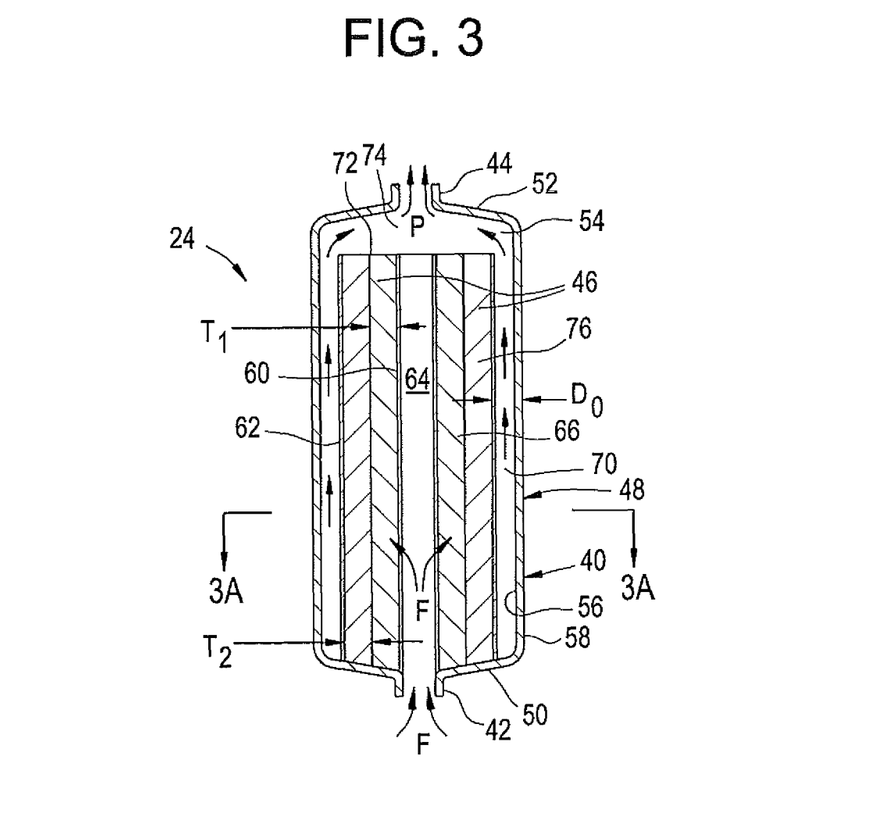
FIG. 3 illustrates a cross-sectional view of a conventional radial reactor capable of producing styrene from the reaction of toluene and formaldehyde, the radial reactor containing a catalyst bed including multiple layers consistent with one embodiment of the present invention.
Figure 3A:
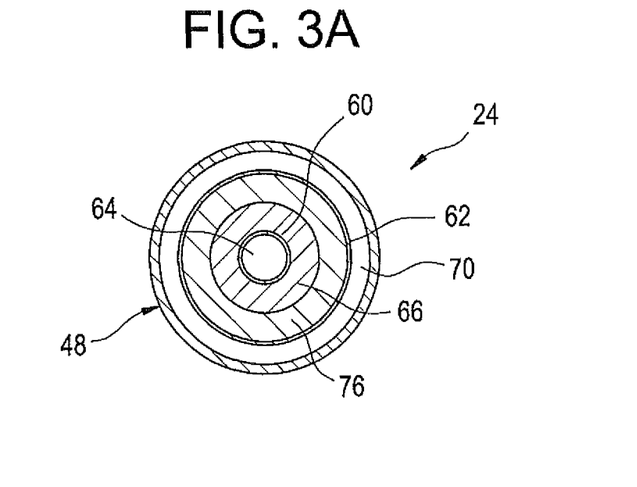
FIG. 3A illustrates a top cross-sectional view along the cutting plane of the embodiment shown in FIG. 3.

Optionally, as illustrated in FIGS. 3 and 3A, the catalyst bed (46) comprises at least two vertical layers. More specifically, the catalyst bed (46) comprises a vertical inner layer (66) mounted along the inner cavity wall (60) and proximate the inner passage (64) and a vertical outer layer (76) mounted between the inner layer (66) and the outer cavity wall (62). Optionally, a third cavity wall may be mounted between the vertical inner and outer layers to retain the catalyst materials in their respective layers. Each vertical layer (66, 76) has a predetermined thickness, $T_1$ and $T_2$, respectively, and the thickness of each layer may vary depending on the application. With the multilayer catalyst bed, as the feedstream is fed into the inner passage (64) it is forced initially through the vertical inner layer (66) of catalyst material and then through the vertical outer layer (76) of catalyst material before exiting into the outer annulus (70). The vertical inner and outer layers may contain the same composition of catalyst particles. Optionally, the composition of catalyst particles in the inner layer may differ from the composition of catalyst particles in the outer layer.

The operating conditions of the reactors and separators can be system specific and can vary depending on the feedstream composition and the composition of the product streams. The radial reactor for the reaction of toluene and formaldehyde will operate at elevated temperatures and may contain a basic or neutral catalyst system. The temperature can range in a non-limiting example from 250° C. to 750° C., optionally from 300° C. to 500° C., optionally from 375° C. to 450° C. The radial reactor will operate from subatmospheric pressures to elevated pressures. The pressure can range in a non-limiting example from 0.1 atm to 70 atm, optionally from 0.1 atm to 35 atm, optionally from 0.1 atm to 10 atm, optionally from 0.1 atm to 5 atm.

Figure 4:
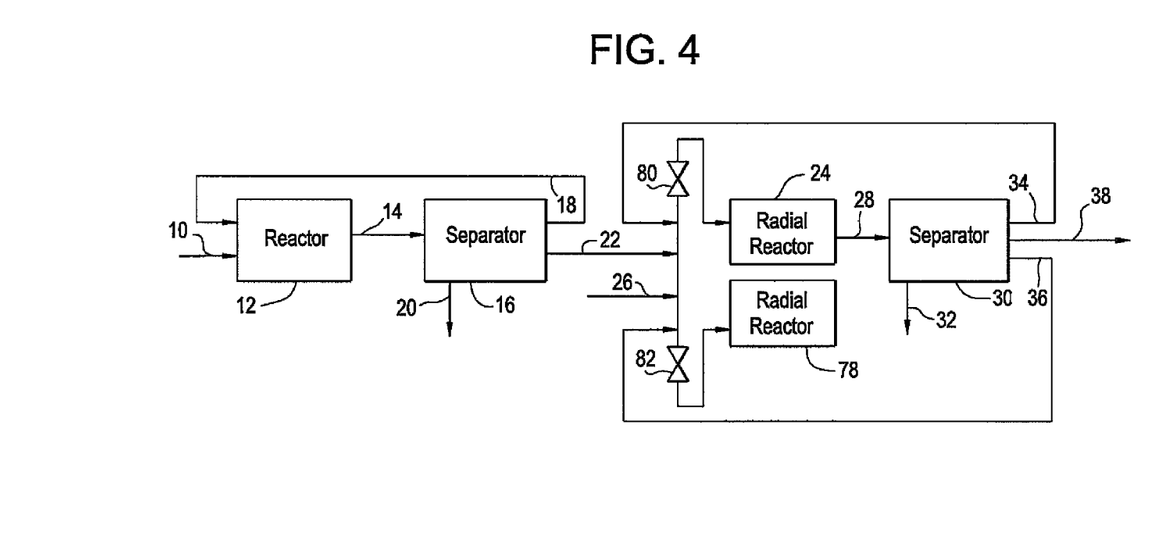
FIG. 4 illustrates a flow chart for the production of styrene by the reaction of formaldehyde and toluene, wherein the formaldehyde is first produced in a separate reactor by either the dehydrogenation or oxidation of methanol and is then reacted with toluene in a primary radial reactor to produce styrene, the primary radial reactor connected in parallel with a secondary radial reactor.

FIG. 4 is a simplified flow chart illustrating an alternate embodiment of FIG. 1, wherein the styrene production process may be operated to provide a continuous reaction system. In this embodiment, a first reactor (12) is either a dehydrogenation reactor or an oxidation reactor. The first reactor is designed to convert the first methanol feed (10) into formaldehyde. The gas product (14) of the first reactor is then sent to a gas separation unit (16) where the formaldehyde is separated from any unreacted methanol and unwanted byproducts. Any unreacted methanol (18) can then be recycled back into the first reactor (12). The byproducts (20) are separated from the stream containing formaldehyde (22).

In one embodiment, the first reactor (12) is a dehydrogenation reactor that produces formaldehyde and hydrogen and the separation unit (16) is a membrane capable of removing hydrogen from the product stream (14).

In an alternate embodiment, the first reactor (12) is an oxidative reactor that produces product stream (14) including formaldehyde and water. The product stream (14) including formaldehyde and water can then be sent to a second reactor (24) without a separation unit (16).

The formaldehyde feed stream (22) is then reacted with a feed stream of toluene (26) in the second reactor (24), which is a primary radial reactor in the embodiment illustrated in FIG. 3. The toluene and formaldehyde react to produce styrene. The product (28) of the radial reactor (24) may then be sent to an optional separation unit (30) where any unwanted byproducts (32) such as water can be separated from the styrene, unreacted formaldehyde and unreacted toluene. Any unreacted formaldehyde (34) and the unreacted toluene (36) can be recycled back into the radial reactor (24). A styrene product stream (38) can be removed from the separation unit (30) and subjected to further treatment or processing if desired.

As the toluene and formaldehyde react over the catalyst, the catalyst gradually deactivates over time resulting in spent catalyst. The spent catalyst must be regenerated or removed from the primary radial reactor and replaced with new or regenerated catalyst in order to maintain efficient styrene production. In the embodiment shown in FIG. 4, a secondary radial reactor (78) containing fresh catalyst is connected in parallel with the primary radial reactor (24). Upon deactivation of the catalyst in the primary radial reactor, the primary radial reactor can be taken offline and the secondary catalyst can be brought online. In FIG. 4, a nonlimiting example is shown wherein the primary radial reactor may be taken offline and the secondary catalyst may be brought online by manipulation of a primary valve (80) and a secondary valve (82). Optionally, a plurality of radial reactors may be connected in parallel. The catalyst in the primary radial reactor may be regenerated or removed and replaced with regenerated or fresh catalyst material. Upon deactivation of the catalyst in the secondary radial reactor, the valves are manipulated such that the secondary radial reactor is taken offline and the primary radial reactor, containing fresh or regenerated catalyst, is brought back online. This process may be repeated, thus resulting in a continuous reaction system for the production of styrene. Such a system is commonly referred to as swing reactors. Optionally, the radial reactor may operate with a continuous reaction and with continuous catalyst regeneration in a manner wherein the catalyst is continuously added and removed for regeneration. For example catalyst can be added to the top of the inner annulus (68) in some manner (not shown), flow downward through the inner annulus (68) and removed from the inner annulus (68) in some manner (not shown).

Figure 5:
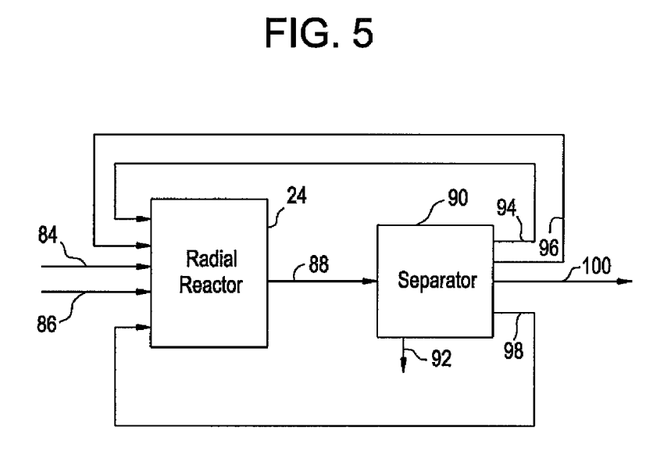
FIG. 5 illustrates a flow chart for the production of styrene by the reaction of formaldehyde and toluene, wherein methanol and toluene are fed into a reactor, wherein the methanol is converted to formaldehyde and the formaldehyde is reacted with toluene to produce styrene.

FIG. 5 is a simplified flow chart of another embodiment of the styrene process discussed above. A methanol containing feed stream (84) is fed along with a feed stream of toluene (86) in a radial reactor (24). The methanol reacts with a catalyst in the radial reactor to produce formaldehyde. The toluene and formaldehyde then react to produce styrene. The product (88) of the reactor (24) may then be sent to an optional separation unit (90) where any unwanted byproducts (92) can separated from the styrene, unreacted methanol, unreacted formaldehyde and unreacted toluene. Any unreacted methanol (94), unreacted formaldehyde (96) and the unreacted toluene (98) can be recycled back into the radial reactor (24). A styrene containing product stream (100) can be removed from the separation unit (90) and subjected to further treatment or processing if desired.

The operating conditions of the reactors and separators will be system specific and can vary depending on the feedstream composition and the composition of the product streams. The radial reactor (24) for the reactions of methanol to formaldehyde and toluene with formaldehyde will operate at elevated temperatures and may contain an acidic, basic or neutral catalyst system. The temperature can range in a non-limiting example from 250° C. to 750° C., optionally from 300° C. to 500° C., optionally from 375° C. to 450° C. The radial reactor will operate from subatmospheric pressures to slightly elevated pressures. The reaction pressure can range in a non-limiting example from 0.1 atm to 70 atm, optionally from 0.1 atm to 35 atm, optionally from 0.1 atm to 10 atm, optionally from 0.1 atm to 5 atm.

In at least one embodiment, the radial reactor comprises a reaction zone, which includes the inner annulus and catalyst bed, as the main reaction site. In the coupling reaction of toluene with a $C_1$ source such as formaldehyde, the conversion of toluene has been observed to be highest at the earliest segment of the contact time between the fresh or regenerated catalyst and the reactants. The residence time, or contact time, of catalyst and hydrocarbons in the radial reactor needed for substantial completion of the reaction may vary as needed for the specific reactor design and throughput design. It has been determined that as the contact time increases, the likelihood of undesirable reactions increases, such as the hydrogenation of styrene to ethylbenzene. Thus, it is desirable to decrease the contact time in the present invention. In one embodiment, the contact time is less than 10 minutes. In optional embodiments, the contact time is less than 8 minutes, less than 6 minutes, less than 4 minutes, less than 2 minutes, less than 1 minute, or less than 30 seconds.

In the coupling reaction of toluene with a $C_1$ source such as formaldehyde, it is also observable that the relationship between contact time and pressure drop is linear. Thus, it is desirable for the pressure drop over the catalyst to be less than 20 psi. In optional embodiments, the pressure drop is less than 10 psi, less than 5 psi, less than 1 psi.

Any suitable space velocity, within the short reaction time parameters of the present invention, can be considered to be within the scope of the invention. The space velocity can generally range from about 0.1 $h^{-1}$ to about 40 $h^{-1}$, optionally from about 1 $h^{-1}$ to about 20 $h^{-1}$, optionally from about 2 $h^{-1}$ to about 10 $h^{-1}$, optionally from about 3 $h^{-1}$ to about 7 $h^{-1}$. This range is an indication of possible space velocities, such as for a radial reactor. Of course altering the catalyst composition, the amount of inert material, etc. can alter the space velocity outside of this range. The space velocity ranges given are not limiting on the present invention and any suitable condition is considered to be within the scope of the invention.

Modification of the physical character of the catalyst to enhance the diffusion rate of the reactants to active sites and the products away from active sites would be advantageous to the conversion of reactants and selectivity of desired products. Another means of improvement of side chain alkylation selectivity can be to inhibit overly basic sites, such as for example with the addition of a boron compound. Such catalyst modifications include depositing the active components onto an inert substrate, optimizing the size of catalyst particles, and imparting void areas throughout the catalyst. Increasing porosity and/or increasing the surface area of the catalyst can accomplish this optimization.

Improvement in side chain alkylation selectivity may be achieved by treating a molecular sieve zeolite catalyst with proper chemical compounds to inhibit the external acidic sites and minimize aromatic alkylation on the ring positions. Another means of improvement of side chain alkylation selectivity can be to impose restrictions on the catalyst structure to facilitate side chain alkylation. In an embodiment, the catalyst used in an embodiment of the present invention is an acidic, basic or neutral catalyst. In an embodiment the catalyst has predominately basic characteristics but can still contain weakly acidic sites.

The catalytic reaction systems suitable for this invention can include one or more of the zeolite or amorphous materials modified for side chain alkylation selectivity. A non-limiting example can be a zeolite promoted with one or more of the following: Co, Mn, Ti, Zr, V, Nb, K, Cs, Ga, B, P, Rb, Ag, Na, Cu, Mg, Fe, Mo, Ce, and combinations thereof.

Zeolite materials suitable for this invention may include aluminosilicate-based zeolites and amorphous compounds such as faujasites, mordenites, etc. Silicate-based zeolites are made of alternating $SiO_2$ and $MO_x$ tetrahedral, where M is an element selected from the Groups 1 through 16 of the Periodic Table (new IUPAC). These types of zeolites have 4-, 6-, 8-, 10-, or 12-membered oxygen ring channels. An example of zeolites of this invention can include faujasites. Other suitable zeolite materials include X-type and Y-type zeolites. In a more specific embodiment, the zeolite is an X-type zeolite.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" as used herein is not meant to indicate that this component is necessarily inactive, while the other metals and/or promoters are the active species. On the contrary, the substrate can be an active part of the catalyst. The term "substrate" would merely imply that the substrate makes up a significant quantity, generally 10% or more by weight, of the entire catalyst. The promoters individually can range from 0.01% to 60% by weight of the catalyst, optionally from 0.01% to 50%. If more than one promoters are combined, they together generally can range from 0.01% up to 70% by weight of the catalyst. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can include an alumina or aluminate framework as a support. Upon calcination these elements can be altered, such as through oxidation which would increase the relative content of oxygen within the final catalyst structure. The combination of the catalyst of the present invention combined with additional elements such as a binder, extrusion aid, structured material, or other additives, and their respective calcination products, are included within the scope of the invention.

In one embodiment, the catalyst can be prepared by combining a substrate with at least one promoter element. Embodiments of a substrate can be a molecular sieve, from either natural or synthetic sources. Zeolites and zeolite-like materials can be an effective substrate. Alternate molecular sieves also contemplated are zeolite-like materials the crystalline silicoaluminophosphates (SAPO) and the aluminophosphates (ALPO).

The present invention is not limited by the method of catalyst preparation, and all suitable methods should be considered to fall within the scope herein. Particularly effective techniques are those utilized for the preparation of solid catalysts. Conventional methods include co-precipitation from an aqueous, an organic or a combination solution-dispersion, impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

The prepared catalyst can be ground, pressed, sieved, shaped and/or otherwise processed into a form suitable for loading into a radial reactor. The radial reactor can be any type known in the art to make catalyst particles. Optionally an inert material, such as quartz chips, can be used to support the catalyst bed and to place the catalyst within the bed. Depending on the catalyst, a pretreatment of the catalyst may, or may not, be necessary. For the pretreatment, the radial reactor can be heated to elevated temperatures, such as 200° C. to 900° C. with an air flow, such as 100 mL/min, and held at these conditions for a length of time, such as 1 to 3 hours. Then, the radial reactor can be brought to the operating temperature of the radial reactor, for example 300° C. to 550° C., or optionally down to any other desired temperature. The radial reactor can be kept under an inert purge, such as under a nitrogen or helium purge.

Radial reactors capable of the elevated temperature and the range of pressures as described herein, and capable of enabling contact of the reactants with the catalyst, can be considered within the scope of the present invention. Embodiments of the particular reactor system may be determined based on the particular design conditions and throughput, as by one of ordinary skill in the art, and are not meant to be limiting on the scope of the present invention.

The toluene and formaldehyde coupling reaction may have a toluene conversion percent greater than about 0.01 wt %. In an embodiment the toluene and formaldehyde coupling reaction is capable of having a toluene conversion percent in the range of from 0.05 wt % to 5 wt %. In a further embodiment the toluene and formaldehyde coupling reaction is capable of having a toluene conversion in the range of from 2 wt % to 4 wt %.

In an embodiment the toluene and formaldehyde coupling reaction is capable of selectivity to styrene greater up to about 85 wt %. In another embodiment, the toluene and formaldehyde coupling reaction is capable of selectivity to styrene in the range of from 60 wt % to 80 wt %. In an embodiment the toluene to formaldehyde coupling reaction is capable of selectivity to ethylbenzene in the range of from 10 wt % to 50 wt %. In another embodiment, the toluene to formaldehyde coupling reaction is capable of selectivity to ethylbenzene in the range of from 15 wt % to 35 wt %. In an embodiment, the ratio of selectivity to styrene and selectivity to ethylbenzene ($S_{sty}:S_{EB}$) is in the range of from 5:1 to 5:3.

The term "conversion" refers to the percentage of reactant (e.g. toluene) that undergoes a chemical reaction.

$X_{Tol}$=conversion of toluene (mol %)=($Tol_{in}$−$Tol_{out}$)/$Tol_{in}$

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "regenerated catalyst" refers to a catalyst that has regained enough activity to be efficient in a specified process. Such efficiency is determined by individual process parameters.

The term "selectivity" refers to the relative activity of a catalyst in reference to a particular compound in a mixture. Selectivity is quantified as the proportion of a particular product relative to all other products.

$$S_{Sty}=\text{selectivity of toluene to styrene (mol \%)}=Sty_{out}/Tol_{converted}$$

The term "spent catalyst" refers to a catalyst that has lost enough catalyst activity to no longer be efficient in a specified process. Such efficiency is determined by individual process parameters.

The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

The various embodiments of the present invention can be joined in combination with other embodiments of the invention and the listed embodiments herein are not meant to limit the invention. All combinations of various embodiments of the invention are enabled, even if not given in a particular example herein.

While illustrative embodiments have been depicted and described, modifications thereof can be made by one skilled in the art without departing from the spirit and scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Also, it is within the scope of this disclosure that the embodiments disclosed herein are usable and combinable with every other embodiment disclosed herein, and consequently, this disclosure is enabling for any and all combinations of the embodiments disclosed herein. Other and further embodiments, versions and examples of the invention may be devised without departing from the basic scope thereof and the scope thereof is determined by the claims that follow.

What is claimed is:

1. A process for making styrene comprising:
reacting toluene with a $C_1$ source comprising formaldehyde over a catalyst in at least one radial reactor to form a product stream comprising styrene, wherein the radial reactor comprises a reaction zone comprising the catalyst, wherein the process is conducted such that an average residence time in the reaction zone of the reactants is less than 60 seconds, wherein the reaction of the toluene and the formaldehyde has a selectivity to styrene ranging from 60 to 80 weight percent; and
wherein the catalyst comprises an X-type zeolite promoted with a promoter selected from the group consisting of Co, Mn, Ti, Zr, V, Nb, Ga, Ag, Na, Cu, Mg, Fe, Mo, Ce, and combinations thereof.

2. The process of claim 1, wherein the $C_1$ source further comprises methanol, formalin, trioxane, methylformcel, paraformaldehyde, methylal, dimethyl ether, or combinations thereof.

3. The process of claim 1, wherein the reaction pressure in the radial reactor is in the range of 0.1 atm to 70 atm.

4. The process of claim 1, wherein the reaction pressure in the radial reactor is in the range of about 0.1 atm to about 10 atm.

5. The process of claim 1, wherein the process is conducted such that the average residence time in the reaction zone of the reactants is less than about 30 seconds.

6. The process of claim 1, wherein the catalyst is promoted with a promoter selected from the group consisting of Cu, Co, Ga, and combinations thereof.

7. The process of claim 1, wherein
the reaction pressure in the radial reactor is in the range of 0.1 atm to 5 atm.

8. The process of claim 1, wherein the reaction of the toluene and the formaldehyde has a selectivity to ethylbenzene ranging from 15 to 35 weight percent.

9. The process of claim 1, wherein the reaction of the toluene and the formaldehyde exhibits a ratio of selectivity to styrene to selectivity to ethylbenzene ranging from 5:1 to 5:3.

10. The process of claim 1, wherein the reaction of the toluene and the formaldehyde has a toluene conversion ranging from 0.05 to 5 weight percent.

11. The process of claim 1, wherein a toluene to $C_1$ source molar ratio ranges from 100:1 to 1:100.

12. The process of claim 1, wherein a pressure drop over the catalyst in the reaction of the toluene and the formaldehyde is less than 20 psi.

13. The process of claim 1, wherein prior to the reaction of the toluene and the formaldehyde, the catalyst is pretreated in the radial reactor by:
heating the radial reactor to an elevated temperature ranging from 200 to 900° C. with an air flow;
maintaining the elevated temperature and the air flow in the radial reactor for from 1 to 3 hours; and
bringing the radial reactor from the elevated temperature to an operating temperature ranging from 300 to 550° C.

14. A process for making styrene comprising:
reacting toluene with a $C_1$ source comprising formaldehyde over a catalyst in at least one radial reactor to form a product stream comprising styrene;
wherein the radial reactor comprises a reaction zone comprising the catalyst, wherein the process is conducted such that an average residence time in the reaction zone of the reactants is less than 60 seconds, a reaction pressure in the radial reactor is in the range of 0.1 atm to 10 atm, and a pressure drop over the catalyst in the reaction of the toluene and the formaldehyde is less than 5 psi; and
wherein the reaction of the toluene and the formaldehyde has a selectivity to styrene ranging from 60 to 80 weight percent, a ratio of selectivity to styrene to selectivity to ethylbenzene ranging from 5:1 to 5:3, and a toluene conversion ranging from 0.05 to 5 weight percent; and
wherein the catalyst comprises an X-type zeolite promoted with a promoter selected from the group consisting of Co, Mn, Ti, Zr, V, Nb, Ga, Ag, Na, Cu, Mg, Fe, Mo, Ce, and combinations thereof.

15. A process for making styrene comprising:
reacting toluene with a $C_1$ source comprising formaldehyde over a catalyst in at least one radial reactor to form a product stream comprising styrene;
wherein the radial reactor comprises a reaction zone comprising the catalyst, wherein the process is conducted such that an average residence time in the reaction zone of the reactants is less than about 30 seconds, a reaction pressure in the radial reactor is in the range of 0.1 atm to 5 atm, and a pressure drop over the catalyst in the reaction of the toluene and the formaldehyde is less than 1 psi; and
wherein the reaction of the toluene and the formaldehyde has a selectivity to styrene ranging from 60 to 80 weight percent, a ratio of selectivity to styrene to selectivity to ethylbenzene ranging from 5:1 to 5:3, and a toluene conversion ranging from 0.05 to 5 weight percent; and
wherein the catalyst comprises an X-type zeolite promoted with a promoter selected from the group consisting of Co, Mn, Ti, Zr, V, Nb, Ga, Ag, Na, Cu, Mg, Fe, Mo, Ce, and combinations thereof.

* * * * *